United States Patent [19]
Ohno et al.

[11] Patent Number: 5,876,738
[45] Date of Patent: Mar. 2, 1999

[54] ANTIFUNGAL PHYLLOSILICATE

[75] Inventors: Yasuharu Ohno; Manabu Tanase; Kouji Sugiura; Tosirou Hirukawa; Hideki Katou, all of Aichi, Japan

[73] Assignee: Toagosei Co., Ltd., Tokyo, Japan

[21] Appl. No.: 957,337

[22] Filed: Oct. 24, 1997

[30] Foreign Application Priority Data

Oct. 29, 1996 [JP] Japan .................................... 8-303825
Oct. 30, 1996 [JP] Japan .................................... 8-303974

[51] Int. Cl.$^6$ ............................. A01N 25/34; A01N 25/00
[52] U.S. Cl. ............................................ 424/404; 424/405
[58] Field of Search ....................................... 424/404, 405

[56] References Cited

U.S. PATENT DOCUMENTS 5,730,996  3/1998  Beall et al. .............................. 424/405

OTHER PUBLICATIONS

Derwent Abstract No. 007910922 of JP 1115958, May 1998.

*Primary Examiner*—Raymond Henley, III
*Attorney, Agent, or Firm*—Davidson, Davidson & Kappel, LLC

[57] ABSTRACT

The present invention provides an antifungal phyllosilicate comprising a phyllosilicate carrying a triazole-type antifungal organic compound between the layers thereof, and an antibacterial and antifungal composition comprising the antifungal phyllosilicate and an inorganic antibacterial agent.

16 Claims, No Drawings

ANTIFUNGAL PHYLLOSILICATE

BACKGROUND OF THE INVENTION

1. Field of the Invention

The present invention relates to an antifungal phyllosilicate having excellent water resistance, chemical resistance, heat resistance, prolonged antifungal property and weather resistance. The antifungal phyllosilicate of the invention is useful as an antifungal agent which can be incorporated into a molding material such as resins (e.g., rubber and plastics) or which can be coated onto the surface of a molded article to impart an antifungal property to the molding material or the molded article. The present antifungal phyllosilicate can also be blended with an inorganic antibacterial agent to provide an antibacterial and antifungal composition excellent in water resistance, chemical resistance, heat resistance, a prolonged antifungal property and an antibacterial property, particularly excellent in an antifungal property by which the germination of spores of fungi can be inhibited.

2. Description of Prior Art

Up to date, various types of organic and inorganic antibacterial and antifungal agents have been developed for imparting an antifungal property to a desired material.

As the organic antibacterial and antifungal agents, there have been known quaternary ammonium compounds such as benzalkonium chloride; sulfur-containing benzimidazole compounds such as 2,4-thiazolylbenzimidazole; bisthiocyanate compounds such as methylene bisthiocyanate; quinolinol compounds such as 8-quinolinol; alcohols such as ethanol; aldehyde compounds such as formalin; phenol compounds such as cresol; carboxylic acid compounds such as sorbic acid; and so on.

As the inorganic antibacterial and antifungal agents, there have been known those comprising an antibacterial metal ion, such as silver ion, copper ion and zinc ion, carried in a material such as active carbon, apatite and zeolite.

However, the conventional organic and inorganic antibacterial and antifungal agents have some disadvantages to be improved.

For example, the conventional organic antibacterial and antifungal agents are generally poor in heat resistance. Therefore, when incorporated into plastics or fibers under heating, they tend to cause discoloration or blowing of the resultant products or tend to be evaporated or degraded during the incorporation and, as a result, a satisfactory antibacterial or antifungal effect of the agents can not be achieved. In addition, the organic antibacterial and antifungal agents are also poor in chemical resistance and show a relatively high solubility to any solvent. Therefore, when used with a solvent for molding an article, they tend to be leached out from the resultant article, which causes the decrease in antibacterial or antifungal effect of the agents and gives some fear of adverse influence to a human body. For these reasons, the organic antibacterial and antifungal agents are limited in their practical applications.

On the other hand, although the conventional inorganic antifungal agents are excellent in heat resistance and chemical resistance, they exhibit a poorer antifungal effect relative to the antibacterial effect.

For the purpose of improving the above-mentioned disadvantages of the conventional antibacterial and antifungal agents, there has been proposed an antibacterial and antifungal phyllosilicate obtained by substituting at least a part of ion-exchangeable metal ions of a phyllosilicate by an antibacterial and antifungal organic compound (see Japanese Patent Application Laid-open No. 4-292410).

However, the present inventors have found that the phyllosilicate obtained by the above-mentioned technique has some disadvantages such as discoloration and poor weather resistance, and that the organic compound present in the phyllosilicate causes such disadvantages.

SUMMARY OF THE INVENTION

In these situations, the present inventors have made an intensive and extensive study for improving the above-mentioned disadvantages of the conventional antibacterial and antifungal agent. As a result, they have found that a phyllosilicate carrying a particular antifungal organic compound between its layers shows excellent water resistance, chemical resistance, heat resistance, prolonged antifungal property and weather resistance and, therefore, have achieved the present invention.

Accordingly, the object of the present invention is to provide an antifungal phyllosilicate comprising a phyllosilicate carrying a triazole-type antifungal organic compound between its layers. In the antifungal phyllosilicate, at least a part of ion-exchangeable metal ions of the phyllosilicate may be substituted by calcium ion or hydrogen ion.

Another object of the present invention is to provide an antibacterial and antifungal composition comprising the above-mentioned antifungal phyllosilicate and an inorganic antibacterial agent. The composition may further comprise a metal oxide.

DETAILED DESCRIPTION OF THE INVENTION

The present invention will be illustrated in detail below.

Antigungal organic compound

One aspect of the present invention is to provide an antifungal phyllosilicate comprising a phyllosilicate carrying a triazole-type antifungal organic compound between its layers.

Specific examples of the triazole-type antifungal organic compound include the followings (whose custom names are bracketed): α-[2-(4-chlorophenyl)ethyl]-α-(1,1-dimethylethyl)-1H-1,2,4-triazol-1-yl-ethanol [tebconazole], 1-(4-chlorophenoxy)-3,3-dimethyl-1-(1H-1,2,4-triazol-1-yl)-2-butanone [triadimefon], β-(4-chlorophenoxy)-α-(1,1-dimethylethyl)-1H-1,2,4-triazole-1-ethanol [triadimenol], 1-[[2-(2,4-dichlorophenyl)-4-propyl-1,3-dioxolan-2-yl]methyl]-1H-1,2,4-triazole [propiconazole], 1-[[2-(2,4-dichlorophenyl)-4-ethyl-1,3-dioxolan-2-yl]methyl]-1H-1,2,4-triazole [etaconazole] and (RS)-2-(2,4-dichlorophenyl)-1-(1H-1,2,4-triazol-1-yl)hexan-2-ol [hexaconazole].

In the present invention, the antifungal organic compounds may be used singly or in combination of two or more of them.

Phyllosilicate

The phyllosilicate used in the present invention is those known in the art and any natural or synthetic type may be used as long as it has a layer structure in which crystalline layer units are laminated on each other.

Preferred phyllosilicates are clay minerals including, for example, those of smectite group such as montmorillonite, beidellite, hectorite and saponite; those of vermiculite group; those of mica group such as illite, muscovite, phlogopite and biotite; those of brittle mica group such as margarite and clintonite; those of chlorite group; those of kaolin group such as kaolinite and halloysite; and those of serpentine group such as antigorite.

Other phyllosilicates preferably used in the present invention include sodium phyllosilicates such as magadiite, kenyaite, kanemite, makatite, ilerite; calcium phyllosilicates such as tobermorite; synthetic micas in which at least a part of hydroxide groups, are substituted by fluoride; and so on.

Among them, especially preferred are those of smectite group and vermiculite group, synthetic micas and substituted forms thereof in which a part or all of hydroxide groups are substituted by fluoride.

In the antifungal phyllosilicate of the present invention, the phyllosilicate used is not particularly limited in its particle size, moisture content, ion exchange capacity and color. However, when used for incorporation into resins (e.g., plastics, rubbers) or fibers, the phyllosilicate preferably has an average particle diameter of not more than 10 $\mu$m, preferably 0.1 to 7 $\mu$m, and more preferably having a narrow and uniform particle size distribution. In addition, for the achievement of satisfactory antifungal effect of the present antifungal phyllosilicate, the phyllosilicate preferably has an cation exchange capacity of not less than 0.1 milli-equivalent per 1 g.

The above-listed phyllosilicates may be used singly. Alternatively, the phyllosilicates may be used in combination of two or more of them to control the release rate of the antifungal organic compound from the phyllosilicates.

In the present invention, a part or all of ion-exchangeable metal ions present in the phyllosilicate may be substituted by other substituent ions. The substituent ions used include, but are not limited to, calcium ion, hydrogen ion, lithium ion, sodium ion, magnesium ion and so on. Among them, particularly preferred are calcium ion and hydrogen ion.

When the ion-exchangeable metal ions in the phyllosilicate are substituted by other substituent ions, the phyllosilicate is preferably treated with an excess amount of the substituent ions and then fully washed with a solvent such as pure water and ethanol. If the treatment or washing is insufficient, unsubstituted ion-exchangeable metal ions remain between the layers of the phyllosilicate and, as a result, the resultant antifungal phyllosilicate would not exhibit a sufficient weather resistance. In the present invention, the phyllosilicate is particularly preferred in which at least 90% of the ion-exchangeable metal ions are substituted.

In the present invention, the lowest amount of the triazole-type antifungal organic compound to be carried in the phyllosilicate is preferably not less than 0.1 part by weight (hereinafter, simply referred to as "part"), preferably not less than 1 part, and particularly preferably not less than 5 parts, based on 100 parts of the antifungal phyllosilicate. If the amount is too small, the antifungal effect of the antifungal phyllosilicate would decrease. On the other hand, the highest amount of the triazole-type antifungal organic compound to be carried may vary depending on the types of the phyllosilicate and the antifungal organic compound used. However, if the amount is too high, discoloration of the antifungal phyllosilicate would occur and it would be difficult to control the release rate of the antifungal organic compound from the layers of the phyllosilicate. Accordingly, it is preferred to determine an appropriate highest amount of the antifungal organic layer by conducting a preliminary examination.

The triazole-type antifungal organic compound can be introduced into the phyllosilicate in any manner by contacting the antifungal organic compound with the phyllosilicate. The antifungal organic compound may be introduced into the phyllosilicate in any state such as a solid state, a liquid state or a gaseous state.

For example, when an antifungal organic compound in a liquid state is used, the compound is mixed with the phyllosilicate under stirring and then dried and pulverized to obtain an antifungal phyllosilicate carrying the antifungal organic compound therein. Alternatively, a solution of the antifungal organic compound in a solvent having a high solubility to the antifungal organic compound is mixed with the phyllosilicate under stirring, and then filtered and washed, followed by drying and pulverization to obtain an antifungal phyllosilicate carrying the antifungal organic compound therein. The mixture of the antifungal organic compound and the phyllosilicate may be subjected to drying and pulverization without washing.

The conditions for preparation of the present antifungal phyllosilicate are not particularly limited, and may be varied depending on the types of the antifungal organic compound and the phyllosilicate used and the amount of the antifungal organic compound to be carried in the phyllosilicate. Typically employed are a solvent having a pH of 0.1–13, the time for stirring of 0.5–72 hr, the stirring temperature of from room temperature to about 40°–120° C., and the stirring rate of 10–1000 rpm/min.

Inorganic anitbacterial agent:

Another aspect of the present invention is to provide an antibacterial and antifungal composition comprising the above-mentioned antifungal phyllosilicate and an inorganic antibacterial agent having excellent water resistance, chemical resistance, heat resistance, prolonged antifungal effect and antibacterial property, particularly having excellent antifungal property by which the germination of spores of fungi can be inhibited.

The inorganic antibacterial agent used in the present antibacterial and antifungal composition comprises an inorganic compound carrying therein an antibacterial metal ion which is known to exhibit antibacterial property, such as silver ion and copper ion.

Specific examples of the inorganic compound to carry the antibacterial metal ion include the followings: inorganic adsorbents such as active carbon, activated alumina and silica gel; and inorganic ion exchangers such as zeolite, hydroxyapatite, zirconium phosphate, titanium phosphate, potassium titanate, hydrous bismuth oxide, hydrous zirconium oxide and hydrotalcite-type compounds.

The antibacterial metal ion can be introduced into the inorganic compound in any known manner, for example, by physical or chemical adsorption of the metal ion to the inorganic compound; ion exchange reaction between the metal ion and the ion-exchangeable ion in the inorganic compound; use of a binding agent for binding the metal ion to the inorganic compound; intercalation of the metal ion into the inorganic compound; and formation of thin layer containing the metal ion onto the inorganic compound by vacuum evaporation, dissolution/deposition reaction and thin film formation such as sputtering.

Among the above-mentioned inorganic compounds, the inorganic ion exchangers are preferred because they can carry an antibacterial metal ion strongly. Preferred inorganic ion exchangers are quadrivalent metal phosphate-type ion exchangers represented by formula (1):

$$A_b M^2(PO_4)_3 \cdot nH_2O \tag{1}$$

wherein A is at least one ion selected from the group consisting of an alkaline metal ion, an alkaline earth metal ion, an ammonium ion and a hydrogen ion; $M^2$ is a quadrivalent metal; n is an integer of $0 \leq n \leq 6$; b is a positive number, provided that mb=1 wherein m is the valence number of A.

Particularly preferred inorganic antibacterial agents are those represented by formula (2):

$$M^1_a A_b M^2(PO_4)_3 \cdot nH_2O \tag{2}$$

wherein $M^1$ is at least one metal ion selected from the group consisting of silver, copper, zinc, tin, mercury, lead, iron, cobalt, nickel, manganese, arsenic, antimony, bismuth, barium, cadmium and chromium ions; each of A, $M^2$ and n is the same as defined in formula (1); each of a and b is a positive number, provided that ka+mb=1 wherein k is the valence number of $M^1$ and m is the valence number of A.

The compound of formula (2) is an amorphous compound or a crystalline compound belonging to space group R3c, in which the constituent ions form together a three-dimensional network structure.

In the above-mentioned phosphate-type antibacterial agents, preferred are those of crystalline forms having a three-dimensional network structure because of their less discoloration under exposure to light.

In formula (2), the candidates for $M^1$ in formula (2) are metals which have been known to exhibit an antibacterial effect. Among them, silver is the most effective metal capable of enhancing the antifungal, antibacterial and algae-proof properties as well as safety of the antibacterial agent.

In formula (2), A represent at least one ion selected from the group consisting of an alkaline metal ion, an alkaline earth metal ion, an ammonium ion and a hydrogen ion. Preferred examples of the ion include alkaline metal ions such as lithium ion, sodium ion and potassium ion; alkaline earth metal ions such as magnesium ion and calcium ion; and a hydrogen ion. Among them, in view of stability and availability at low cost of the agent, particularly preferred ions are potassium, lithium, sodium, ammonium and hydrogen ions.

In formula (2), $M^2$ is a quadrivalent metal ion. Preferred examples of the quadrivalent ion include zirconium, titanium and tin ions. Among them, in view of safety of the agent, zirconium and titanium ions are particularly preferred.

Specific examples of the phosphate-type antibacterial agent of formula (2) include the followings:

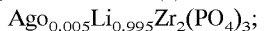$Ag_{0.005}Li_{0.995}Zr_2(PO_4)_3$;
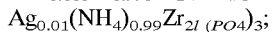$Ag_{0.01}(NH_4)_{0.99}Zr_{2/(PO_4)_3}$;
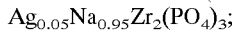$Ag_{0.05}Na_{0.95}Zr_2(PO_4)_3$;
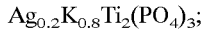$Ag_{0.2}K_{0.8}Ti_2(PO_4)_3$;
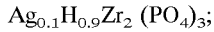$Ag_{0.1}H_{0.9}Zr_2(PO_4)_3$;
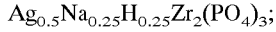$Ag_{0.5}Na_{0.25}H_{0.25}Zr_2(PO_4)_3$;
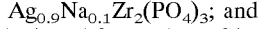$Ag_{0.9}Na_{0.1}Zr_2(PO_4)_3$; and substituted forms thereof in which Ag is substituted with a substituent selected from the group consisting of Zn, Mn, Ni, Pb, Hg, Sn and Cu so that the charge amount of Ag ion becomes equal to that of the substituent based on 1 mole of the agent.

These phosphate-type antibacterial agents can be synthesized in a conventional manner such as calcination process, wet process, hydrothermal process, or the like.

For the antibacterial and antifungal composition of the present invention, the value of a in formula (2) is preferably larger to achieve a higher antibacterial effect. However, the value of a not less than 0.001 can achieve a satisfactory antibacterial effect of the composition. On the other hand, when the value of a is less than 0.001, it tends to be difficult to achieve a satisfactory antibacterial effect of the composition for prolonged period of time. For these reasons, it is preferred for the value of a in formula (2) to be not less than 0.01. When the antibacterial and antifungal composition is incorporated into a resin for molding an article, for the purpose of providing a satisfactory moldability and strength of the molded article and achieving a satisfactory antibacterial effect for a long period of time, it is preferred to set the value of a in the formula (2) at not less than 0.03 and to reduce the amount of the compound of formula (2) to be added relative to the amount of the resin. However, for an economical reason, the value of a in formula (2) is preferably not more than 0.7.

The phosphate-type antibacterial agent is stable against exposure to light, and also causes no change in its structure and composition after heating to 500° C. and even after heating to 800°–1100° C., and also is stable to irradiation with UV ray without any discoloration.

In addition, the phosphate-type antibacterial agent shows no change in its skeletal structure even when contacted with water of liquid state or dissolved in an acidic solution. Accordingly, unlike the conventional antibacterial agents, the phosphate-type antibacterial agent of the present invention has no limitation in practical applications including processing and storage of molded articles, as well as heating temperature and shading conditions.

In the present invention, the antibacterial and antifungal composition may further comprise at least one metal oxide selected from the group consisting of zinc oxide and titanium dioxide to enhance the antibacterial effect of the present composition.

Any natural or synthetic zinc oxide may be used, which is not particularly limited in its nature and properties and the method for production thereof. In general, various types of zinc oxide may be used such as those conventionally used for inks, fillers, UV absorbents, ceramic materials, cosmetics, dental materials, photosensitive materials, pharmaceuticals, catalysts, electronic materials, fluorescent substances and battery cells, as well as so-called "zinc white" conventionally used as pigment.

Any natural or synthetic titanium dioxide may be used, which may be non-crystalline or crystalline and is not particularly limited in its nature and properties and the method for production thereof. The crystalline titanium dioxide can be classified into three classes, i.e., anatase, rutile and brookite, and any of them may be used in the present invention. However, in view of easy availability in an industrial scale, anatase and rutile are preferred. In general, various types of titanium dioxide can be used such as those used for inks, cosmetics, pharmaceuticals, glazes, dental materials, organic titanium materials, ceramic materials, abrasive materials (polishing materials), reinforcing materials, catalysts and electronic materials, as well as those used as pigments.

The metal oxide used is not particularly limited in its particle size and form of the particle. However, in view of dispersibility into a resin, the metal oxide preferably has an average particle diameter of not more than 10 $\mu$m and takes the form of cubic, rectangular, spherical or needle-like form.

It is also possible to use the metal oxide further treated on its surface to increase the dispersibility and to decrease the surface activity thereof. The surface treatment of the metal oxide may be carried out by either wet process or dry process. There is no limitation in the surface-treating agent to be used in the process. However, water-soluble salts of aluminum, zinc and silica are preferably used.

In the antibacterial and antifungal composition of the present invention, the metal oxide may be additionally used in combination with the inorganic antibacterial agent in an amount of 5 to 90 parts based on 100 parts of the total amount of the inorganic antibacterial agent and the metal oxide. If used in an amount of less than 5 parts, the enhancement of the antibacterial effect resulted from the combination of the metal oxide and the inorganic antibacterial agent would be hardly achieved. On the other hand, if used in an amount of more than 90 parts, the inorganic antibacterial agent would decrease in its own antibacterial property.

Furthermore, it is also preferred that the inorganic antibacterial agent contain the antibacterial metal ion in an amount of not less than 0.5% by weight based on the total amount of the inorganic antibacterial agent and the metal oxide.

Amount of the inorganic antibacterial agent:

The inorganic antibacterial agent may be preferably used in an amount of 1 to 90 parts, more preferably 10 to 80 parts, and especially preferably 30 to 70 parts based on 100 parts of the total amount of the inorganic antibacterial agent and the antifungal phyllosilicate. If used in an amount of less than 1 part, a satisfactory antibacterial effect would not be achieved. On the other hand, if used in an amount of more than 90 parts, a satisfactory antifungal effect would not be achieved.

When the metal oxide is used in combination with the inorganic antibacterial agent, the metal oxide used is added in an amount such that the total amount of the both compounds falls within the range stated for the inorganic antibacterial agent.

In the antibacterial and antifungal composition of the present invention, the antifungal phyllosilicate and the inorganic antibacterial agent can be blended in any manner as long as the both components can be blended homogeneously.

Applications:

The antifungal phyllosilicate according to the present invention is useful as an antifungal agent which can be incorporated into various materials to impart an antifungal effect to the materials.

Examples of the materials to be incorporated with the present antifungal phyllosilicate include resins including rubbers such as silicone rubber and acrylic rubber; plastics such as poly(vinyl chloride), polyolefins, polyurethane, ABS, polystyrene, poly(vinyl acetate) and polycarbonates; and so on.

Alternatively, the present antifungal phyllosilicate can also be applied onto the surface of a substrate (e.g., metals, plastics, ceramics) in a form of a suspension in a liquid medium (e.g., water, an organic solvent) in the presence or absence of a binder by means of a conventional application method (e.g., spray coating, coater coating, dipping coating, brushing coating, roll coating), to thereby form a film on the substrate which can prevent the growth of fungi on the surface of the substrate.

The present antifungal phyllosilicate may also be incorporated into various molding base materials to form a molded article. The molding may be conducted in a conventional manner and the molded article may take any form including fiber, film, sheet, plate or block.

The present antifungal phyllosilicate may be incorporated into the base material in an amount of 0.1 to 30 parts, more preferably from 0.5 to 10 parts based on 100 parts of the base material.

Specific examples of the applications of the material or molded article incorporated with the present antifungal phyllosilicate include fibrous articles such as towels, carpets and curtains; leathers; electrical apparatuses such as refrigerators, washing machines, tableware dryers, cleaners, air conditioners, televisions and telephones; building materials such as wall papers, tiles, bricks, concretes, screws and masonry joints; household miscellaneous goods such as washbasins, teeth brushes, brooms, hosepipes, mules, garbage boxes and scrubbing brushes; kitchenware goods such as chopping boards, triangular garbage disposals and kitchen knives; toiletry goods; various coating materials, paints and adhesives; and so on.

The antifungal phyllosilicate according to the present invention is excellent in prolonged antifungal property, and exhibits no discoloration even when exposed to light and, therefore, shows excellent weather resistance.

Accordingly, the antifungal phyllosilicate of the present invention is useful as an antifungal agent useful for wide variety of applications including molded articles comprising various rubbers and plastics (e.g., films and sheets) and various fibers, papers, leathers, paints, adhesives, heat insulating materials and cauking materials and so on.

The present invention will be illustrated in more detail with reference to the following examples, which should not be construed to limit the scope of the present invention.

EXAMPLES

Reference Example 1

Preparation of phyllosilicate

To 1.0 l of a 0.1 mol/l aqueous solution of $CaCl_2$ was suspended 100.0 g of a phyllosilicate, a Na-type synthetic fluoromica, by stirring at 300 rpm at 60° C. for 4 hr to thereby substitute the ion-exchangeable sodium ions in the phyllosilicate by calcium ions. After filtration of the suspension, the filter cake was washed with ion-exchanged water until the Na ions present in the washing solution reached 1 ppm or less. The filter cake thus washed was dried at 100° C. and then pulverized to obtain a Ca-type phyllosilicate having an average particle diameter of 5 $\mu$m.

Example 1

Preparation of antifungal phyllosilicate

To 7.5 g of a triazole-type antifungal organic compound, α-[2-(4-chlorophenyl)ethyl]-α-(1,1-dimethylethyl)-1H-1,2,4-triazole-1-yl-ethanol, was added 42.5 g of the Ca-type phyllosilicate obtained in Reference Example 1. To the resultant mixture was further added 40 g of pure water. The resultant mixture was fully mixed in a mortar, dried at 115° C. and then pulverized, to thereby obtain white-colored antifungal phyllosilicate A.

Reference Example 2

Into 2.4 l of a 0.05 mol/l aqueous solution of HCl was suspended 100.0 g of a metal-type phyllosilicate, a Na-type synthetic fluoromica, by stirring at 400 rpm at room temperature for 24 hr. The resultant suspension was filtered. The filter cake was washed with ion-exchanged water until the Na ions present in the washing solution reached 1 ppm or less. The filter cake thus washed was dried at 100° C. and then pulverized to obtain an H-type phyllosilicate having an average particle diameter of 5 $\mu$m.

Example 2

To 7.5 g of a triazole-type antifungal organic compound, α-[2-(4-chlorophenyl)ethyl]-α-(1,1-dimethylethyl)-1H-1,2,4-triazole-1-yl-ethanol was added 42.5 g of the H-type phyllosilicate obtained in Reference Example 2. To the resultant mixture was further added 40 g of pure water. The resultant mixture was fully mixed in a mortar, dried at 115° C. and then pulverized, to thereby obtain white-colored antifungal phyllosilicate B.

To 7.5 g of a triazole-type antifungal organic compound, α-[2-(4-chlorophenyl)ethyl]-α- (1,1-dimethylethyl)-1H-1,2, 4-triazole-1-yl-ethanol, was added 42.5 g of a Na-type synthetic fluoromica. To the resultant mixture was further added 40 g of pure water. The resultant mixture was fully mixed in a mortar, dried at 115° C. and then pulverized, to thereby obtain white-colored antifungal phyllosilicate C.

Comparative Examples 1–3:

Substantially the same procedures as in Examples 1 to 3 were respectively repeated, except that a non-triazole-type antifungal organic compound, 2-(4-thiazolyl) benzimidazole, was used as the antifungal organic compound, to obtain corresponding antifungal phyllosilicates D, E and F, respectively.

Evaluation of properties:

Preparation of test pieces 1–3

To 147.5 g of the vinyl chloride resin composition having a formula shown in Table 1 was added 2.5 g of each of the antifungal phyllosilicates A–C obtained above. The resultant mixture was kneaded homogeneously by a heat roller at 150° C. for 5 min., and subsequently molded with a press (170° C., 100 kg/cm²) into a sheet of 2 mm thick, 12 cm wide and 10 cm long. The resultant sheet was cut into a small piece of 2 cm square for use in the following evaluation. In this manner, test pieces 1, 2 and 3 corresponding to antifungal phyllosilicates A, B and C, respectively, were prepared.

Preparation of comparative test pieces 1–3

Substantially the same procedure as for the preparation of test pieces 1–3 was repeated, except that the antifungal phyllosilicates D, E and F were used instead of antifungal phyllosilicates A, B and C, to obtain corresponding comparative test pieces 1, 2 and 3.

Preparation of comparative test piece 4

Substantially the same procedure as for the preparation of test piece 1 was repeated, except that, instead of antifungal phyllosilicate A, 0.3 g of a triazole-type antifungal organic compound, α-[2-(4-chlorophenyl)ethyl]-α-(1,1-dimethylethyl)-1H-1,2,4-triazole-1-yl-ethanol was added to 149.7 g of the resin composition of Table 1, in which the 0.3 g of the triazole-antifungal phyllosilicate A corresponds to the net amount of the antifungal organic compound added to the resin composition in the preparation of test piece 1. In this manner, comparative test piece 4 was obtained.

TABLE 1

| Component | Blend Amount [part(s)] |
|---|---|
| Vinyl chloride resin*¹ | 100 |
| Dioctyl phthalate (as plastisizer)*² | 40 |
| Epoxydized soy bean oil*³ (as plastisizer and stabilizer) | 2 |
| Ca—Zn-type complex stabilizer*⁴ | 0.7 |
| Phosphite-type stabilizer*⁵ | 0.5 |

*¹"Ts1100", manufactured and sold by TOAGOSEI CO., LTD.
*²manufactured and sold by Tohorika Kogyo K.K.
*³"300K", manufactured and sold by DAICEL CHEMICAL INDUSTRIES, LTD.
*⁴"Adekastab 37", manufactured and sold by ASAHI DEANKA KOGYO K.K.
*⁵"Adekastab 102", manufactured and sold by ASAHI DEANKA KOGYO K.K.

Evaluation of antifungal property

Each of test pieces 1–3 and comparative test pieces 1–4 was immersed into hot water at 50° C. for a day or seven days, and was then evaluated on the change over time in antifungal effect in the following manner.

That is, in the examination of the antifungal property, two kinds of fungi, black koji-mold (*Aspergillus niger*) and black mold (*Cladosporium cladospolies*), were used as test fungi. The examination was conducted by placing a test piece or a comparative test piece taken out from the hot water on day 1 and day 7 onto a Sabouraud's agar medium and measured for the width of the growth inhibition zone formed on the medium after 14 days.

Evaluation of weather resistance

Each of test pieces 1–3 and comparative test pieces 1–4 was evaluated on its weather resistance using a weatherometer ("UVCON", manufactured and sold by ATLAS). The test program of the weatherometer took 8 hr for a cycle and comprised a first step for irradiating UV ray having a wavelength of not more than 350 nm at 60° C. for 4 hr and a second step for allowing to stand in an atmosphere of not less than 95% of humidity at 40° C. for 4 hr. For each test piece, the color given after 0 cycle of the test program ($L_1$, $a_1$, $b_1$) and the color given after three cycles of the test program ($L_2$, $a_2$, $b_2$) were respectively determined using a differential colorimeter ("SΣ-80" type differential colorimeter, manufactured and sold by Nippon Denshoku Kogyo K. K.) and the color difference (ΔE) was calculated according to the following equation:

$$\Delta E=[(L_1-L_2)^2+(a_1-a_2)^2+(b_1-b_2)^2]^{1/2} \quad (1).$$

The results obtained are shown in Table 2 below.

Table 2 demonstrates that the molded articles containing the present antifungal phyllosilicate carrying a triazole-type antifungal organic compound showed a less decrease in antifungal effect even after washed for a long period of time in comparison with the molded articles containing an antifungal organic compound without a phyllosilicate, and showed a less discoloration and better weather resistance in comparison with the molded article containing an antifungal phyllosilicate carrying an antifungal organic compound other than triazole-type one.

TABLE 2

| | Growth inhibition zone (mm) | | | | Color |
|---|---|---|---|---|---|
| | Black koji-mold | | Black mold | | |
| difference | Day 1 | Day 7 | Day 1 | Day 7 | (ΔE) |
| Test piece 1 | 3–5 | 3–4 | 2–3 | 1–2 | 2.1 |
| Test piece 2 | 3–5 | 3–4 | 3–4 | 2–3 | 1.3 |
| Test piece 3 | 4–6 | 3–5 | 3–4 | 2–3 | 1.2 |
| C. Test piece 1 | 0–1 | 0–1 | 1–2 | 1–2 | 10.6 |
| C. Test piece 2 | 1–2 | 1–2 | 1–2 | 1–2 | 11.5 |
| C. Test piece 3 | 0–1 | 0–1 | 1–2 | 1–2 | 10.9 |
| C. Test piece 4 | 1–2 | — | 1–2 | — | 2.3 |

In the table, "—" means no formation of growth inhibition zone on the agar medium.

Examples 4–6

Preparation of antibacterial and antifungal composition

Each of antifungal phyllosilicates A, B and C obtained in Examples 1, 2 and 3 was added to an equivalent weight of the following antibacterial inorganic agent [5] and then blended each other homogeneously using a small Henschel mixer to obtain corresponding antibacterial and antifungal compositions a, b and c:

$Ag_{0.53}Na_{0.17}H_{0.30}Zr_2$ [5]

Evaluation of antifungal efffect 1

Determination of minimum inhibitory concentration (MIC)

Each of antibacterial and antifungal compositions a–c obtained in Examples 4–6 and antifungal phyllosilicates A–C obtained in Examples 1–3 was added to 8 ml of a potato-dextrose medium in concentrations of 500, 250, 125 and 67.5 ppm. Onto each of the medium were plated spores of a fungus. After 1 week, the antifungal effect of each composition and each phyllosilicate was evaluated by observing the growth of the fungus on the medium. In this evaluation test, Black koji-mold (*Aspergilluys niger*) and black mold (*Cladosporium cladospolis*) were used as test fungi.

The results of MIC determined for black koji-mold and black mold are shown in Table 4 below, wherein the symbols have the following meanings:

TABLE 4

| Type of fungi | Black mold | | | | Black koji-mold | | | |
|---|---|---|---|---|---|---|---|---|
| Concentration (ppm) | 400 | 200 | 100 | 50 | 400 | 200 | 100 | 50 |
| Ex. 4 | ○ | ○ | ○ | ○ | ○ | ○ | ○ | ○ |
| Ex. 5 | ○ | ○ | ○ | ○ | ○ | ○ | ○ | ○ |
| Ex. 6 | ○ | ○ | ○ | ○ | ○ | ○ | ○ | ○ |
| Ex. 1 | ○ | X | X | X | ○ | ○ | ○ | X |
| Ex. 2 | ○ | ○ | X | X | ○ | ○ | ○ | X |
| Ex. 3 | ○ | X | X | X | ○ | ○ | ○ | X |

○: growth of fungi was inhibited;
X: growth of fungi was observed.

Evaluation on antifungal effect 2

Determination of the number of spores by wrap method

Substantially the same procedure as for preparation of test piece 1 was repeated using antibacterial and antifungal compositions a–c of Examples 4–6 to obtain corresponding test pieces 4–6. Onto each of test pieces 4–6 and test pieces 1–3 prepared above was added dropwise 100 μl of a suspension of spores of a fungus containing 0.05% malt extract (concentration of spores: $4.5 \times 10^4$/ml). The resultant test pieces was wrapped with a wrapping sheet (2.5 cm square) tightly, kept in an atmosphere of 90% of humidity at 25° C. for 48 hr, and determined on the change in the number of spores before and after wrapping. In this evaluation test, black koji-mold (*Aspergillus niger*) was used as a test fungus.

The results are shown in Table 5 below.

Evaluation of antifungal effect 3

Evaluation by halo method

Each of test pieces 1–6 was immersed into hot water at 50° C. for a day or seven days, and was then evaluated on the change over time in antifungal effect in the following manner.

That is, in the examination of the antifungal effect, black koji-mold (*Aspergillus niger*) was used as a test fungus. The examination was conducted by placing a test piece taken out from the hot water on day 1 and day 7 on a potato-dextrose agar medium and for the width of the growth inhibition zone formed on the medium after 14 days.

The results are shown in Table 5 below.

Examination of antibacterial effect

The antibacterial effect of each test piece 1–6 was evaluated in the following manner.

That is, *Escherichia coli* was used as a test bacterium and a dilution solution containing about $10^5$ cells/ml of *Escherichia coli* was prepared. Onto each of the test pieces (3 cm square) was added dropwise 100 μl of the dilution solution of *Escherichia coli*. The test pieces thus treated was then wrapped with a wrapping sheet (1.5 cm square) tightly and then kept at 37° C. After incubating them at 37° C. for 0 hr (initial number of cells: $2.6 \times 10^5$ cells/ml) and 6 hr, the living cells remaining on the surface of the test piece was washed with a medium for determination of cell number (SCDLP liquid medium). The washing solution thus obtained was used as a test solution. The test solution was determined on the number of living cells by a pour-plate culture method using the medium for determination of cell number (37° C., for 2 days) and then calculated in terms of the number of living cells per 1 ml of the medium. In this method, the reference cell number was $8.3 \times 10^4$ cells/ml and the blank cell number was $4.1 \times 10^4$ cells/ml.

The results are also shown in Table 5.

TABLE 5

| Test Piece | Wrap method (number of Spores/ml) | Halo method day 1 | Halo method day 7 | Antibacterial (number of living cells/ml) | Total evaluation rank |
|---|---|---|---|---|---|
| 4 | $1.1 \times 10^3$ | ○ | ○ | $<10^2$ | A |
| 5 | $<10^2$ | ○ | ○ | $<10^2$ | A |
| 6 | $8.0 \times 10^2$ | ○ | ○ | $<10^2$ | A |
| 1 | $3.0 \times 10^4$ | ○ | ○ | $2.7 \times 10^4$ | C |
| 2 | $2.8 \times 10^4$ | ○ | ○ | $1.5 \times 10^4$ | C |
| 3 | $3.1 \times 10^4$ | ○ | ○ | $2.9 \times 10^4$ | C |

Note:
In the table above, the symbols have the following meanings:
In Halo method,
○: formation of growth inhibition zone was observed;
X: formation of growth inhibition zone was not observed;
In total evaluation rank,
A: excellent in both antibacterial and antifungal properties;
B: slightly poor in at least one of antibacterial and antifungal properties;
C: poor in at least one of antibacterial and antifungal properties.

Table 5 demonstrates that the present antibacterial and antifungal compositions showed excellent antibacterial and antifungal properties, and did not decrease in antifungal effect even when washed for a long period of time, and showed an excellent prolonged antifungal property. Particularly, the present antibacterial and antifungal compositions are excellent in antifungal property by which the germination of spores of fungi can be inhibited.

What is claimed is:

1. An antifungal phyllosilicate comprising a phyllosilicate carrying a triazole-type antifungal organic compound between the layers thereof, wherein the phyllosilicate further comprises ion-exchangeable metal ions wherein at least a part of the ion-exchangeable metal ions are substituted by calcium ion or hydrogen ion.

2. An antibacterial and antifungal composition comprising a phyllosilicate carrying a triazole-type antifungal organic compound between the layers thereof and an inorganic antibacterial agent.

3. The antibacterial and antifungal composition according to claim 2, which further comprises a metal oxide.

4. An antifungal phyllosilicate according to claim 1 wherein the triazole type antifungal organic compound is selected from the group consisting of α-[2-(4-chlorophenyl) ethyl]-α-(1,1-dimethylethyl)-1H-1,2,4-triazol-1-yl-ethanol, 1-(4-chlorophenoxy)-3,3-dimethyl-1-)1H-1,2,4-triazol-1-yl)-2-butanone, β-(4-chlorophenoxy)-α-(1,1-dimethylethyl)-1H-1,2,4-triazole-1-ethanol, 1-[[2-(2,4-dichlorophenyl)-4-propyl-1,3-dioxolan-2-yl]methyl]-1H-1, 2,4-triazole, 1-[[2-(2,4-dichlorophenyl)-4-ethyl-1,3-dioxolan-2-yl]methyl]-1H-1,2,4-triazole and (RS)-2-(2,4-dichlorophenyl)-1-(1H-1,2,4-triazol-1-yl)hexan-2-ol.

5. An antifungal phyllosilicate according to claim 1 wherein the phyllosilicate comprise clay minerals.

6. An antifungal phyllosilicate according to claim 5 wherein the clay minerals are selected from the group consisting of the smectite group; the vermiculite group; the mica group; the brittle mica group; the kaolin group; and the serpentine group.

7. An antifungal phyllosilicate comprising a phyllosilicate carrying a triazole-type antifungal organic compound between the layers thereof, wherein the phyllosilicate is selected from the group consisting of sodium phyllosilicates, calcium phyllosilicates and synthetic micas in which at least one of the hydroxide groups is substituted by fluoride.

8. An antifungal phyllosilicate according to claim 1 wherein the phyllosilicate particles have an average diameter of not more than 10 microns.

9. An antifungal phyllosilicate according to claim 1 wherein said ion-exchangeable metal ions comprise calcium ion, hydrogen ion, lithium ion, sodium ion and magnesium ion.

10. An antifungal phyllosilicate according to claim 1 wherein at least 90% of the ion-exchangeable metal ions are substituted.

11. The antifungal phyllosilicate according to claim 1 wherein said triazole type antifungal organic compound in the phyllosilicate comprises at least 0.1 part by weight based on 100 parts of the antifungal phyllosilicate.

12. The antifungal phyllosilicate according to claim 1 wherein the triazole type antifungal organic compound is introduced into the phyllosilicate in a solid, liquid or gas phase.

13. An antifungal phyllosilicate according to claim 1, further comprising an inorganic compound to carry the ion-exchangeable metal ions.

14. An antifungal phyllosilicate according to claim 13 wherein the inorganic compound to carry the ion-exchangeable metal ions is selected from the group consisting of inorganics comprising active carbon, activated alumina and silica gel; and selected from the group consisting of inorganic ion exchangers comprising zeolite, hydroxyapatte, zirconium phosphate, titanium phosphate, potassium titanate, hydrous bismuth oxide, hydrous zirconium oxide and hydrotalcite-type compounds.

15. An antifungal phyllosilicate according to claim 1 wherein the ion exchangers are quadrivalent metal phosphate-type ion exchangers represented by the formula $A_b M^2 (PO_4)_3 \cdot nH_2O$, wherein A is at least one ion selected from the group consisting of an alkaline metal ion, an alkaline earth metal ion, an ammonium ion and a hydrogen ion; $M^2$ is a quadrivalent metal; n is an integer of $0 \leq n \leq 6$; b is a positive number, provided that mb=1 wherein m is the valence number of A.

16. An antibacterial and antifungal composition according to claim 2 wherein the antibacterial agent is represented by the formula $M^1_a A_b M^2 (PO_4)_3 \cdot nH_2O$ (2)

wherein $M^1$ is at least one metal ion selected from the group consisting of silver, copper, zinc, tin, mercury, lead, iron, cobalt, nickel, manganese, arsenic, antimony, bismuth, barium, cadmium and chromium ions; A is at least one ion selected from the group consisting of an alkaline metal ion, an alkaline earth metal ion, an ammonium ion and a hydrogen ion; $M^2$ is a quadrivalent metal; n is an integer of $0 \leq n \leq 6$; each of a and b is a positive number, provided that ka+mb=1 wherein k is the valence number of $M^1$ and m is the valence number of A.

* * * * *